United States Patent
Bonnefous et al.

[11] Patent Number: 5,891,039
[45] Date of Patent: Apr. 6, 1999

[54] ULTRASONIC ECHOGRAPHY SYSTEM INCLUDING SEQUENCING MEANS FOR THE EXAMINATION OF ARTERIES

[75] Inventors: Odile Bonnefous, Nogent Sur Marne; Philippe Gendreu, Sucy en Brie, both of France

[73] Assignee: U.S. Philips Corporation, New York, N.Y.

[21] Appl. No.: 996,671

[22] Filed: Dec. 24, 1997

[30] Foreign Application Priority Data

Dec. 31, 1996 [FR] France .................................. 96 16265

[51] Int. Cl.$^6$ .................................................. A61B 8/00
[52] U.S. Cl. ........................... 600/454; 600/465; 600/466
[58] Field of Search .................... 600/437, 454, 600/458, 459, 465, 439, 463, 455, 466

[56] References Cited

U.S. PATENT DOCUMENTS 3,888,238   6/1975   Meindl et al. ........................... 600/455
5,320,105   6/1994   Bonnefous et al. ..................... 600/454
5,471,988   12/1995  Fuijo et al. .............................. 600/439

FOREIGN PATENT DOCUMENTS 0035213   9/1981   European Pat. Off. ........ G01S 15/58

*Primary Examiner*—Marvin M. Lateaf
*Assistant Examiner*—Ali M. Imam
*Attorney, Agent, or Firm*—Dwight H. Renfrew, Jr.

[57] ABSTRACT

An ultrasonic echography system includes a probe (1) which is connected to an echograph provided with a transmission stage (32), receiving and processing stages (34, 38) for ultrasonic echo signals, and a device (21) for displaying images of an artery. The probe (1) is formed by three integral transducers, i.e. a first, central transducer (2) for scanning the artery axially and two lateral, further transducers (3, 4) which are arranged parallel to one another and oriented perpendicularly to the first transducer in order to form transversal sectional images of the artery. The echograph also includes a sequence for sequentially activating each of the three transducers in a cyclical manner.

7 Claims, 3 Drawing Sheets

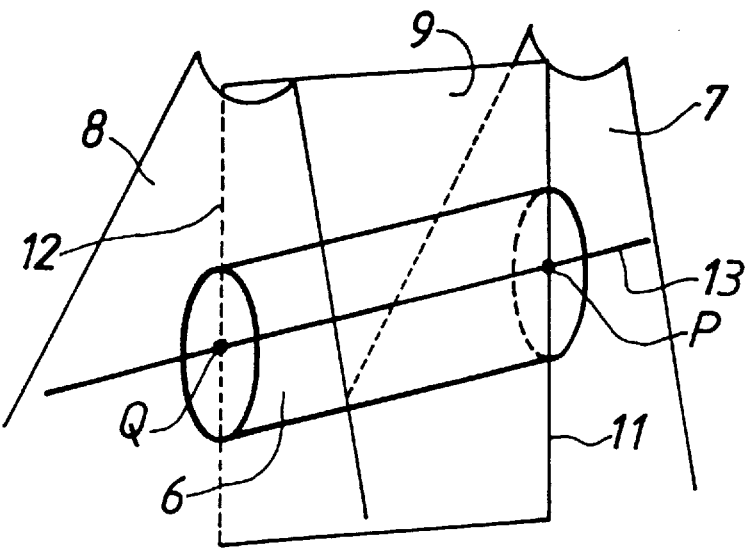
FIG. 2
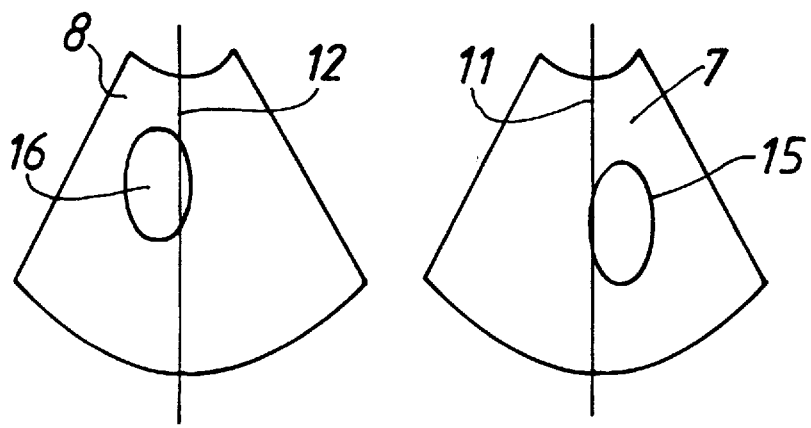
FIG. 3
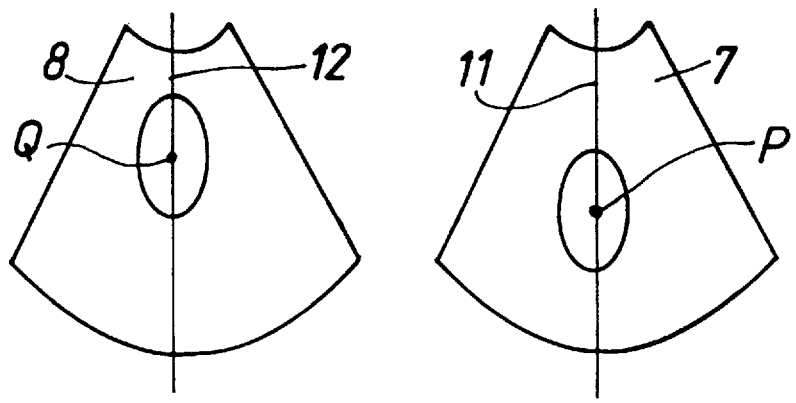

ULTRASONIC ECHOGRAPHY SYSTEM INCLUDING SEQUENCING MEANS FOR THE EXAMINATION OF ARTERIES

BACKGROUND OF THE INVENTION

The invention relates to an ultrasonic echography system for the examination of arteries, including a probe with at least one ultrasonic transducer which is connected to an echograph which is formed by a stage for the transmission of an ultrasonic beam, a stage for the reception and a stage for the processing of ultrasonic signals returned to the probe, and a device for displaying the ultrasonic image of the artery to be examined.

1. Field of the Invention

The invention is used in the field of medical echographic imaging and measurement of physiological parameters.

2. Description of Related Art

Ultrasonic echography has increasingly become an effective means for the visualization of tissues, notably arteries, and nowadays it becomes possible to measure physiological parameters with adequate precision. For the examination of an artery, be it to visualize it in a cross-sectional view or to measure the instantaneous velocity of the blood flow therethrough, the handling of the echographic probe by the operator still remains a delicate operation which could cause incorrect interpretation of the image obtained or become a source of errors during quantitative analysis.

One difficulty encountered in the case of quantitative measurement is the correct positioning of the probe with respect to the axis of the vessel (the artery). Correct positioning is to be understood to mean most often a positioning such that the sectional plane formed by the ultrasonic beam, containing the visualized image, extends through the axis of the artery.

With a view to ensure correct measurement of blood velocities, nowadays given criteria concerning the acquisition of data by means of a conventional probe have been defined, irrespective of whether a linear or a curved probe is concerned. For example, the operator has to carry out a measurement five times for an artery segment considered and retains only the three of said five measurements which are closest to one another. However, this technique is long and rather difficult to carry out and certain operators would like to have a shorter but nevertheless more reliable procedure available; this represents a technical problem to be solved. Given the advances made in respect of speed and calculation precision of the echographic techniques, it is now desirable to improve the imaging of arteries so as to facilitate vascular examination and enable acquisition of more reliable vascular data.

SUMMARY OF THE INVENTION

It is an object of the invention to provide an ultrasonic echography system which enables real-time formation of sectional artery images where the sectional plane of the artery passes through the axis of the latter.

It is another object of the invention to provide an ultrasonic echography system which enables blood flow velocities to be measured with a higher reliability.

It is another object of the invention to provide a probe with ultrasonic transducers which enables, via guiding on the basis of complementary images on a display device, the sectional image of an artery to be adjusted so that it extends through the axis of the latter.

These objects are achieved, and the drawbacks of the prior art are mitigated, in that the ultrasonic echography system of the kind set forth in the preamble is characterized in that said probe consists of an assembly of three integral transducers, a first, central transducer being conceived so as to scan said artery in an axial direction whereas a second and a third, lateral transducer are symmetrically attached to said first transducer and oriented so as to scan the artery substantially transversely in scanning planes extending perpendicularly to the scanning plane of said first transducer, and in that said echograph includes sequencing means for sequentially activating said first, second and third transducers in a cyclical manner.

It is to be noted that probes with two scanning planes are already known for cardiac imaging, for example the probes marketed by the United States company Hewlett Packard for trans-oesophageal examinations.

The display device of the system is designed so as to reproduce three echographic images obtained from the three respective integral transducers. The principal image, which can be followed by a phase for measurement in a part of interest of an artery reproduced thereby, is supplied by the central transducer. The two lateral images, formed in the direction perpendicular to the principal image and parallel to one another, serve to guide the operator during the examination of the relevant artery, allowing the operator to obtain the longitudinal section of maximum surface area if desired, which is generally the case. To this end, in a first step a substantially transversal section of the artery should be formed as an ellipsoid in each lateral image, thus ensuring the acquisition of the principal image along the entire length of the first, central transducer and subsequently, by continuous manipulation of the probe, the centering of these two images in a transversal section in such a manner that the symmetry axis which separates each transversal image plane in the excitation direction, also symmetrically separates each transversal section. These parallel symmetry axes are advantageously materialized on the transversal image planes as a trace on the screen and constitute the intersections of the plane of the central image with each transversal image plane. The latter operation constitutes a kind of preparation for the desired image: it ensures that the principal image supplied by the central transducer contains the axis of the artery. This relative position of the probe with respect to the artery is more attractive for performing an excitation along a principal image line, being an excitation in the pulsed Doppler mode which is intended to supply notably the components of the blood velocities in the excitation direction, the excitation preferably being repeated for the duration of at least one pulsation of the heart.

In a preferred embodiment of the invention, the sequencing means, included in an echograph adapted to the probe having three scanning planes as described above, are formed by two multiplexers which are connected in cascade between said stage for the transmission of ultrasonic signals and said probe, a first multiplexer being provided with first control means for alternation between the signals intended for said first transducer on the one hand and the signals intended for said second and third transducers on the other hand, a second multiplexer being arranged downstream from said first multiplexer and provided with second control means for alternation between the signals intended for said second and third transducers.

The operation sequence of the three transducers in the transmission/receiving mode is cyclically repeated at a frequency which is high enough to enable simultaneous display in real-time of the image supplied by each of the three transducers of the echographic probe on the image display device.

The following description, given with reference to the accompanying drawing and merely by way of example, will offer a better understanding as to how the invention can be carried out.

BRIEF DESCRIPTION OF THE DRAWINGS

FIG. 2 is a perspective view of the three scanning planes of the probe according to the invention, correctly oriented relative to an artery segment.

FIG. 3 illustrates how the images supplied by the lateral transducers enable the probe to be guided to the correct position of FIG. 2.

DETAILED DESCRIPTION OF THE PREFERRED EMBODIMENTS

Figure 1:
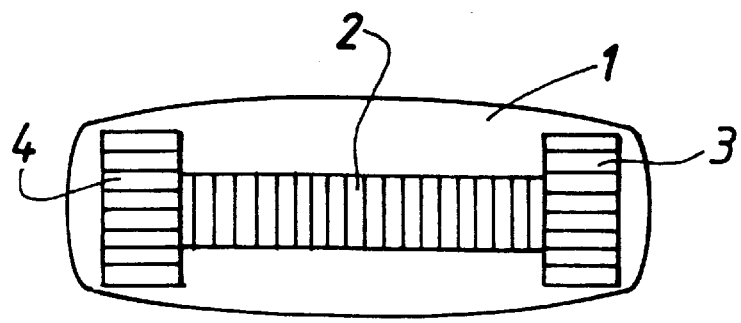
FIG. 1 is a front view of the probe comprising three transducers according to the invention.
Figure 4:
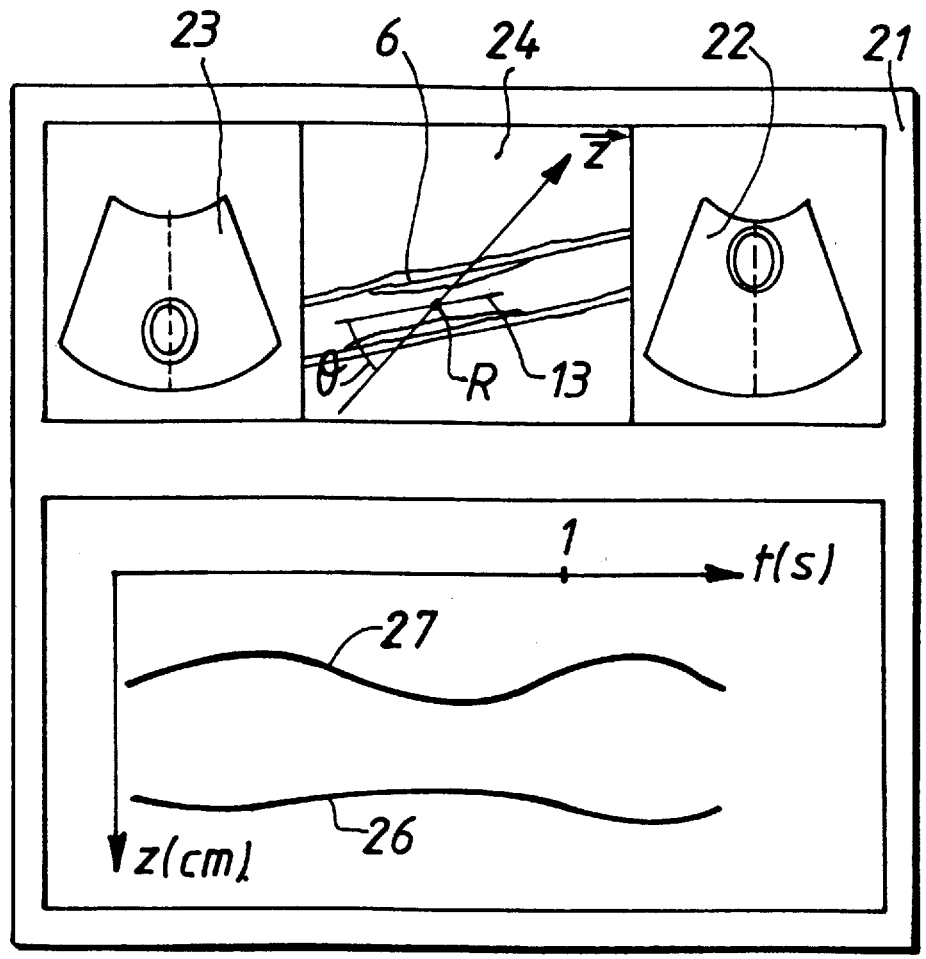
FIG. 4 shows the image display device of the ultrasonic echography system according to the invention.

The echographic probe 1, shown at substantially the scale 2 in FIG. 1, is composed of three transducers, the principal transducer being a central transducer 2 which is designed to scan a blood vessel, generally an artery, in a frontal sectional plane which is referred to as median plane and extends perpendicularly to the plane of the Figure. The echograph operator usually wishes to obtain a longitudinal sectional view of the artery and if the operator is to be able to measure the highest blood velocities within the latter, said median frontal sectional plane should contain the axis of the scanned artery segment which has a length substantially equal to that of the transducer 2. Until now such positioning of the probe is achieved empirically and with a low precision which is no longer in conformity with the capabilities of contemporary echographs. In order to achieve said positioning, according to the invention the transducer 2 is adjoined by two lateral transducers 3 and 4 which are placed at each side so that the assembly consisting of the three transducers 2, 3 and 4 has a frontal symmetry plane (plane 9 in FIG. 2). The transducers 3 and 4 are designed to scan the tissues according to frontal sectional planes which extend mutually in parallel and perpendicularly to the median frontal sectional plane of the transducer 2. The probe shown in FIG. 1 is intended to produce a sectional view of an artery on the screen of a monitor, which view is decomposed into three images as represented at the top of FIG. 4 as will be described in detail hereinafter. Each of the transducers 2, 3 and 4 consists of elementary transducers (represented as small rectangles) which are electronically controlled with appropriate delay rules for the focusing in the transmission as well as the receiving mode, thus enabling a predetermined number of pixels to be obtained in known manner per excitation line, the number of excitation lines being substantially equal to the number of elementary transducers of the transducer. After analog processing, most often followed by digital processing, of the signal, the matrix of points thus obtained constitutes the image displayed on the screen of the monitor.

The transducers 2, 3 and 4 may be of the linear type, such as the Philips type LA7530E, or of the curved type, such as the Philips type CA6414, the latter transducer enabling sectorial images to be obtained. Preferably, the central transducer 2 is of the linear type and the lateral transducers 3 and 4 are of the curved type.

FIG. 2 shows diagrammatically a segment 6 of an artery which is bounded by two lateral planes 7 and 8 and traversed by a median plane 9, being the scanning planes of the transducers 3, 4 and 2, respectively, of FIG. 1. The plane 9 cuts the sectorial sector of the plane 7 at its center in conformity with the line 11, and that of the plane 8 at its center in conformity with the line 12. FIG. 2 shows the optimum position searched for the probe; in this position the axis 13 of the artery 6 intersects the lines 11 and 12 at P and Q, i.e. the points where the plane 9 contains the axis 13. The optimum position is searched by the echograph operator while using the probe as follows:

The search for a part of an artery is started in known manner by forming a section of approximately ellipsoidal shape of said artery in the plane 9 generated by the central transducer 2; subsequently, the trace of this section is made to occupy the entire useful width of the plane 9; at that stage substantially transverse sections of the artery appear in the planes 7 and 8, as represented by 15 and 16 at the top of FIG. 3. The phase for optimum positioning is then terminated moving the probe very slowly so as to center the two traces 15 and 16 on the lines 11 and 12 as shown at the bottom of FIG. 3. The probe being held immobile in this correct position, measurements of the blood velocity can then be performed by means of excitation in the pulsed Doppler mode, including the velocities of echographic targets (globules) present at the center of the artery (the highest velocities), enabling accurate calculation (after integration) of the blood flow as a function of time, for example for the duration of at least one cardiac cycle.

The visualization of the images in the planes 7, 8 and 9 can be implemented as shown at the top of FIG. 4 which shows the screen 21 of a monitor serving as the image display device of the ultrasonic echographic system according to the invention. On said screen the lateral images 22 and 23 of the sectional planes 7 and 8 are shown to both sides of the central image 24 of the sectional plane 9. It will be noted that these two lateral images could also be shown (separately) one above the other.

FIG. 4 shows the scanning configuration of FIG. 2. The image 24 also contains the axis 13 of the artery and the direction (the axis) $\vec{z}$ in which, after the optimum positioning of the probe in known manner, repetitive excitations with ultrasonic pulses will take place for the measurements of the blood velocities. As a result of the invention, the axis 13 and $\vec{z}$ intersect at the point R as is the object of the invention.

The instantaneous velocities measured are the components of the real velocities searched along the axis $\vec{z}$. A multiplicative correction by $1/\cos\theta$ enables switching over from the measured velocities to the real velocities, $\Theta$ being the angle between the axes 13 and $\vec{z}$. The real velocities can be stored in digital form in a memory (not shown). They can also be visualized by means of any known method, for example in the M mode as shown at the bottom of the screen of FIG. 4: the co-ordinates are the time, on the abscissa, and the depth z being a scalar quantity measured perpendicularly to the axis 13 and plotted on the ordinate. FIG. 4 shows traces 26 and 27 which represent the walls of the artery 6 for a period of time which is preferably longer than one cardiac cycle. Between the traces 26 and 27 the blood velocities across the diameter of the artery are visualized by means of colors in conformity with a predetermined code which is generally displayed on the screen (in a manner not shown in FIG. 4).

In order to obtain the above results by means of the three-transducer probe (having three sectional planes) of FIG. 1, it is necessary to adapt the echograph whereto this particular probe is connected. More specifically, the echograph should comprise sequencing means for successively exciting, in a cyclical manner, the transducers 2, 3 and 4 as described hereinafter with reference to FIG. 5. The control of the probe 1 faces the technical problem that the three transducers 2, 3 and 4 cannot be excited at the same time as they could be imagined to be by a respective independent echograph; actually, these three transducers are too close to one another and upon emission as well as reception of ultrasonic signals emitted in the form of three contiguous lobes, such interference would occur that the noisy signals received would not be suitable for use. The solution used to mitigate this drawback consists in activating the three transducers sequentially by means of a single echograph, using multiplexers, in such a manner that only one of the three transducers is active at any instant during operation of the system.

Figure 5:
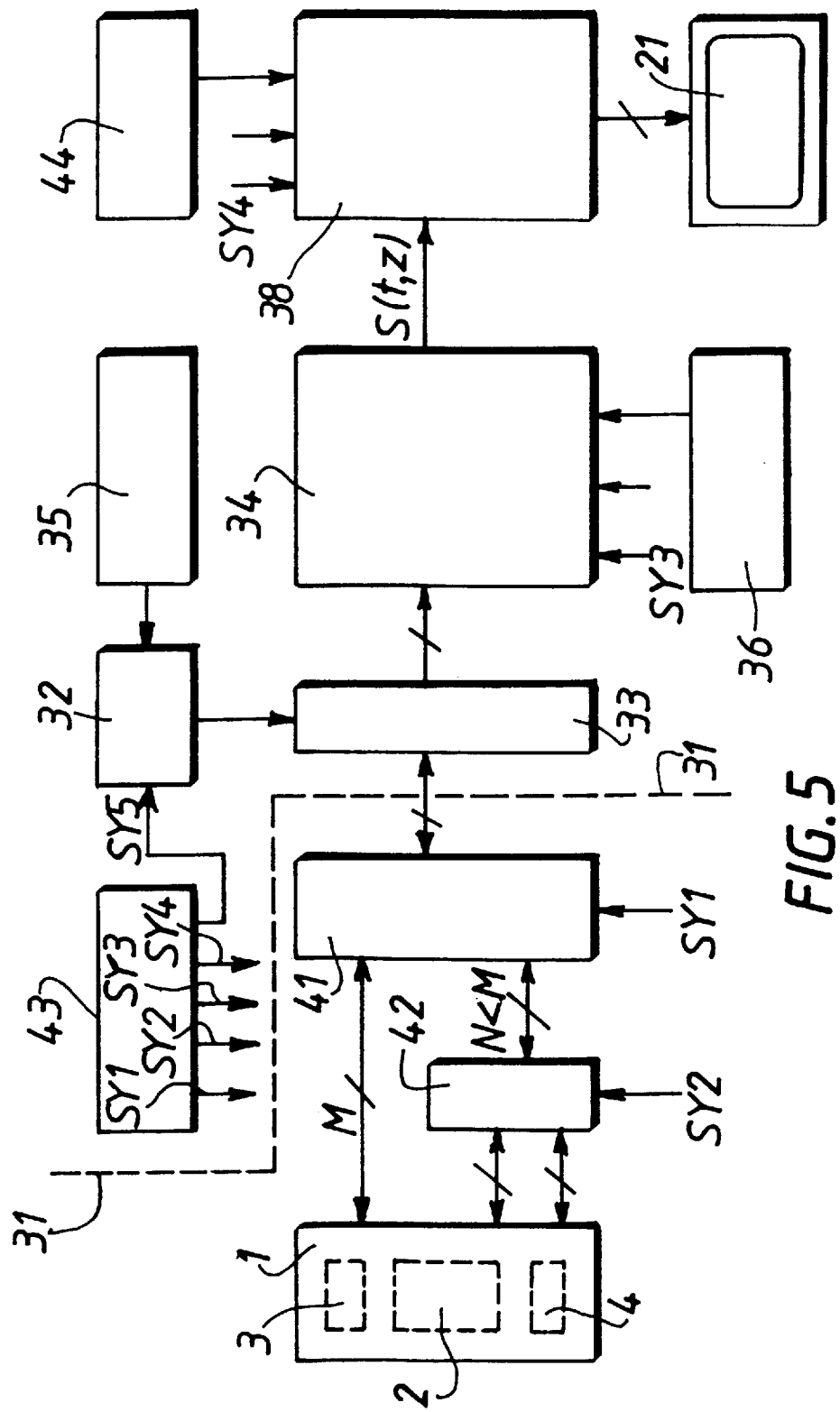
FIG. 5 shows the block diagram of an embodiment of the ultrasonic echography system according to the invention.

The part situated to the right of a dashed line 31 in FIG. 5 is the conventional construction of an echograph being either of the frequential or so-called Doppler type or of the temporal correlation type.

A transmitter stage 32 includes a sequencer which is composed of an oscillator and a frequency divider which controls, at the selected recurrent frequency, a generator whose electric excitation signals are applied to the probe which converts these signals into periodic trains of ultrasonic pulsed signals. A separator 33 between the transmitter stage 32 and the receiving and processing stage 34 (also called front end) is inserted between the probe 1 and said 2 stages 32, 34 and prevents overloading of the receiving circuits by the transmission signals. For a given configuration in the transmission mode, provided to the circuit 32 by a memory 35, for example for the transmission by the transducer 2, the M signals received by the M elementary transducers of the transducer 2 are applied to the circuit 34 which is also referred to as a device for forming channels in the receiving mode. An electronic scanning control (not shown) for the elementary transducers of the transducers 2, or 3, 4, enables selection of the relevant excitation line without displacement of the transducer, said lines being disposed in the same plane, either parallel to one another, as for the transducer 2, or in a diverging manner, as for the transducers 3 and 4. The channel forming device 34 enables, by way of specific delay configurations received from a configuration memory in the receiving mode 36 and imposed on the signals received from the separator 33, as many points to be obtained, by successive focusing, as there are points provided on the selected excitation line 2, 3 or 4 from the nearest point to the most remote point. The channel forming device 34 supplies the downstream signal processing circuits 38, also referred to as the back end, with an output signal S(t,z).

For an echograph provided with a probe comprising only a single transducer, a single plane is cyclically scanned at a frequency of between a few Hz and some tens of Hz, which frequency is sufficiently high to enable a comfortable display on the screen 21, even when the probe is displaced. According to the invention, as soon as the scanning by one of the transducers 2, 3, 4 is terminated in order to supply a first image, the scanning by a second transducer commences, the latter scanning being succeeded directly by the scanning by the third transducer and so on for a cycle of predetermined duration. The scanning periods are equal to T2, T3 and T4 for the transducers 2, 3 and 4, respectively, in such a manner that: T2+T3+T4=T, T being the duration of said cycle, so that the frequency of appearance of the three images on the screen 21 (FIG. 4) equals 1/T. This particular operation is realized by means of two multiplexers 41 and 42 which are suitably synchronized by a clock generator 43.

The multiplexer 41 is controlled (SY1) so as to transmit and receive to the transducer 2 during the period T2 and to the multiplexer 42 during the subsequent period T3+T4. The multiplexer 42 is controlled (SY2) so as to transmit and receive to the transducer 3 during the period T3 and to the transducer 4 during the period T4. During each period T, the circuits 32 and 34 are thus adjusted for transmission and reception for adaptation to each of the three probes by means of synchronizations SY3 and SY5 which are preferably the same, that is to say a first configuration during the period T2 for the operation of the transducer 2 and a second configuration, during the period T3+T4, for the operation of the transducer 3 and subsequently the transducer 4.

The signal S(t,z) thus obtained in a ternary sequence is subsequently processed in the circuit 38 which performs a digital scan conversion so as to reproduce on the screen 21 the images described above with reference to FIG. 4. To this end, it receives a signal from a display configuration memory 44 and a synchronization signal SY4 which enables the display of a new image 22 during the period T3, followed by the display of a new image 23 during the period T4, followed by the display of a new image 24 during the period T2 and so on in a cyclical fashion. Preferably, in order to avoid a butterfly effect on the screen, the duration of each new image is kept equal to T.

It will be noted that echographs are known which include several probes which are dedicated to different applications and that, when one of these probes is chosen by the operator, the configuration of the echograph is automatically established, in 32, 34 and 38, for adaptation to the specific probe; therefore, it is not necessary to describe herein how such adaptation of the echograph to the relevant activated probe can be performed; in other words, it is known that an echographic front end configuration is automatically obtained for a given probe geometry and a given scanning mode. The Philips echograph SD800, adapted as described above, can be used to carry out the invention.

We claim:

1. An ultrasonic echography system for the examination of arteries, including a probe with three ultrasonic transducers which are connected to an echograph which is formed by a first stage for transmission of an ultrasonic beam, a second stage for reception and processing, and a third stage for signal processing of ultrasonic signals returned to the probe, and a device for displaying an ultrasonic image of the artery to be examined, characterized in that said probe consists of an assembly of three integral transducers, a first, central transducer being conceived so as to scan said artery in an axial direction whereas a second and a third, lateral transducer are symmetrically attached to said first transducer and oriented so as to scan the artery substantially transversely in scanning planes extending perpendicularly to the scanning plane of said first transducer, and in that said echograph includes sequencing means for sequentially activating said first, second and third transducers in a cyclical manner.

2. An ultrasonic echography system as claimed in claim 1, characterized in that said sequencing means are formed by two multiplexers which are connected in cascade between said stage for the transmission of ultrasonic signals and said probe, a first multiplexer being provided with first control means for alternation between the signals intended for said first transducer on the one hand and the signals intended for said second and third transducers on the other hand, a second multiplexer being arranged downstream from said first multiplexer and provided with second control means for alternation between the signals intended for said second and third transducers.

3. An ultrasonic echography system as claimed in claim 1, characterized in that said signal processing stage includes processing means for real-time, separate display of the three ultrasonic images obtained from said first, second and third transducers on said display device.

4. A probe comprising ultrasonic transducers for an ultrasonic echography system, characterized in that it consists of an assembly of three integral transducers, a first, central transducer being conceived to scan said artery in an axial direction whereas a second and a third, lateral transducer are symmetrically attached to said first transducer and oriented so as to scan the artery substantially transversely in scanning planes extending parallel to one another and perpendicularly to the scanning plane of said first transducer.

5. A probe comprising ultrasonic transducers as claimed in claim 4, characterized in that it consists of a first, linear central transducer and curved, lateral second and third transducers for acquiring second and third sectorial images.

6. An ultrasonic echography system as claimed in claim 1, characterized in that said sequencing means are formed by two multiplexers which are arranged between said stage for the reception and processing of ultrasonic signals and said probe, a first multiplexer being provided with control means for alternation between the signals intended for said first transducer on the one hand and the signals intended for said second and third transducers on the other hand, a second multiplexer being arranged downstream from said first multiplexer and provided with control means for alternation between the signals intended for said second and third transducers.

7. An ultrasonic echography system as claimed in claim 2, characterized in that said signal processing stage includes processing means for real-time, separate display of the three ultrasonic images obtained from said first, second and third transducers on said display device.

\* \* \* \* \*

UNITED STATES PATENT AND TRADEMARK OFFICE
CERTIFICATE OF CORRECTION

PATENT NO. : 5,891,039
DATED : April 6, 1999
INVENTOR(S) : Bonnefous, et al

It is certified that error appears in the above-identified patent and that said Letters Patent is hereby corrected as shown below:

On the title page, item [22], "Dec. 24, 1997" should read -- Dec. 23, 1997 --

Signed and Sealed this

Sixth Day of June, 2000

Attest:

Q. TODD DICKINSON

*Attesting Officer*            *Director of Patents and Trademarks*